(12) United States Patent
Nishimura et al.

(10) Patent No.: US 11,744,486 B2
(45) Date of Patent: Sep. 5, 2023

(54) BIOMETRIC SYSTEM AND METHOD

(71) Applicants: HIROSHIMA UNIVERSITY, Higashi-Hiroshima (JP); Hitachi, Ltd., Tokyo (JP)

(72) Inventors: Ayako Nishimura, Tokyo (JP); Hirokazu Atsumori, Tokyo (JP); Tsukasa Funane, Tokyo (JP); Akihiko Kandori, Tokyo (JP); Yasuaki Nakamura, Tokyo (JP); Akiko Obata, Tokyo (JP); Yuto Komatsu, Tokyo (JP); Seiji Hama, Higashi-Hiroshima (JP); Toshio Tsuji, Higashi-Hiroshima (JP)

(73) Assignees: Hiroshima University, Hiroshima (JP); Hitachi, Ltd., Tokyo (JP)

( * ) Notice: Subject to any disclaimer, the term of this patent is extended or adjusted under 35 U.S.C. 154(b) by 568 days.

(21) Appl. No.: 17/074,345

(22) Filed: Oct. 19, 2020

(65) Prior Publication Data
US 2021/0121100 A1  Apr. 29, 2021

(30) Foreign Application Priority Data
Oct. 23, 2019  (JP) .................................. 2019-192398

(51) Int. Cl.
*A61B 5/11*  (2006.01)
*A61B 5/00*  (2006.01)
*A61H 3/02*  (2006.01)

(52) U.S. Cl.
CPC .......... *A61B 5/1128* (2013.01); *A61B 5/0077* (2013.01); *A61B 5/112* (2013.01);
(Continued)

(58) Field of Classification Search
CPC ........ A61B 5/1036–1038; A61B 5/112; A61B 5/1128
See application file for complete search history.

(56) References Cited

U.S. PATENT DOCUMENTS 6,231,527 B1 *  5/2001  Sol .................... A61B 5/1038
                                                     600/595
9,149,222 B1 * 10/2015  Zets ................... A61B 5/4023
(Continued)

FOREIGN PATENT DOCUMENTS

JP   H09168529 A  *  6/1997  ............. A43B 13/12
JP   2005081537 A  *  3/2005  ........... A61B 5/1038
(Continued)

OTHER PUBLICATIONS

English machine translation of JP 2019-097995 A. 2023. (Year: 2023).*

*Primary Examiner* — Meredith Weare
(74) *Attorney, Agent, or Firm* — Procopio, Cory, Hargreaves & Savitch LLP

(57) ABSTRACT

A biometric system includes: a camera that captures a subject; a pressure information collection unit that detects a pressure value of at least one sole of the subject; a skeleton direction vector calculation unit that calculates a skeleton direction vector of the subject captured by the camera; a floor reaction force vector calculation unit that calculates a floor reaction force vector on a basis of information on pressure from the pressure information collection unit; and an analysis result output unit that displays, in a superimposing manner, the skeleton direction vector calculated by the skeleton direction vector calculation unit and the floor reaction force vector calculated by the floor reaction force vector calculation unit.

16 Claims, 11 Drawing Sheets

(52) U.S. Cl.
CPC .............. *A61B 5/742* (2013.01); *A61H 3/02* (2013.01); *A61H 2201/5071* (2013.01)

(56) References Cited

U.S. PATENT DOCUMENTS

| | | | | |
|---|---|---|---|---|
| 2011/0239489 | A1* | 10/2011 | Iuchi | A43B 13/141 |
| | | | | 36/25 R |
| 2015/0003687 | A1* | 1/2015 | Utsunomiya | G06V 40/25 |
| | | | | 382/107 |
| 2017/0135608 | A1* | 5/2017 | Pappe | A61B 5/743 |
| 2017/0238845 | A1* | 8/2017 | Wei | A61B 5/1036 |

FOREIGN PATENT DOCUMENTS

| | | | | | |
|---|---|---|---|---|---|
| JP | | 2011220908 | A * | 11/2011 | |
| JP | | 2012161402 | A * | 8/2012 | |
| JP | | 2012-176170 | A | 9/2012 | |
| JP | | 2015061579 | A * | 4/2015 | ............... A61B 5/11 |
| JP | | 2016150193 | A * | 8/2016 | |
| JP | | 2017029516 | A * | 2/2017 | |
| JP | | 2019097995 | A * | 6/2019 | ........... A61B 5/0077 |
| JP | | 7181533 | B2 * | 12/2022 | ........... A61B 5/0077 |
| WO | WO-2011125959 | A1 * | 10/2011 | ............. A43B 13/12 |

\* cited by examiner

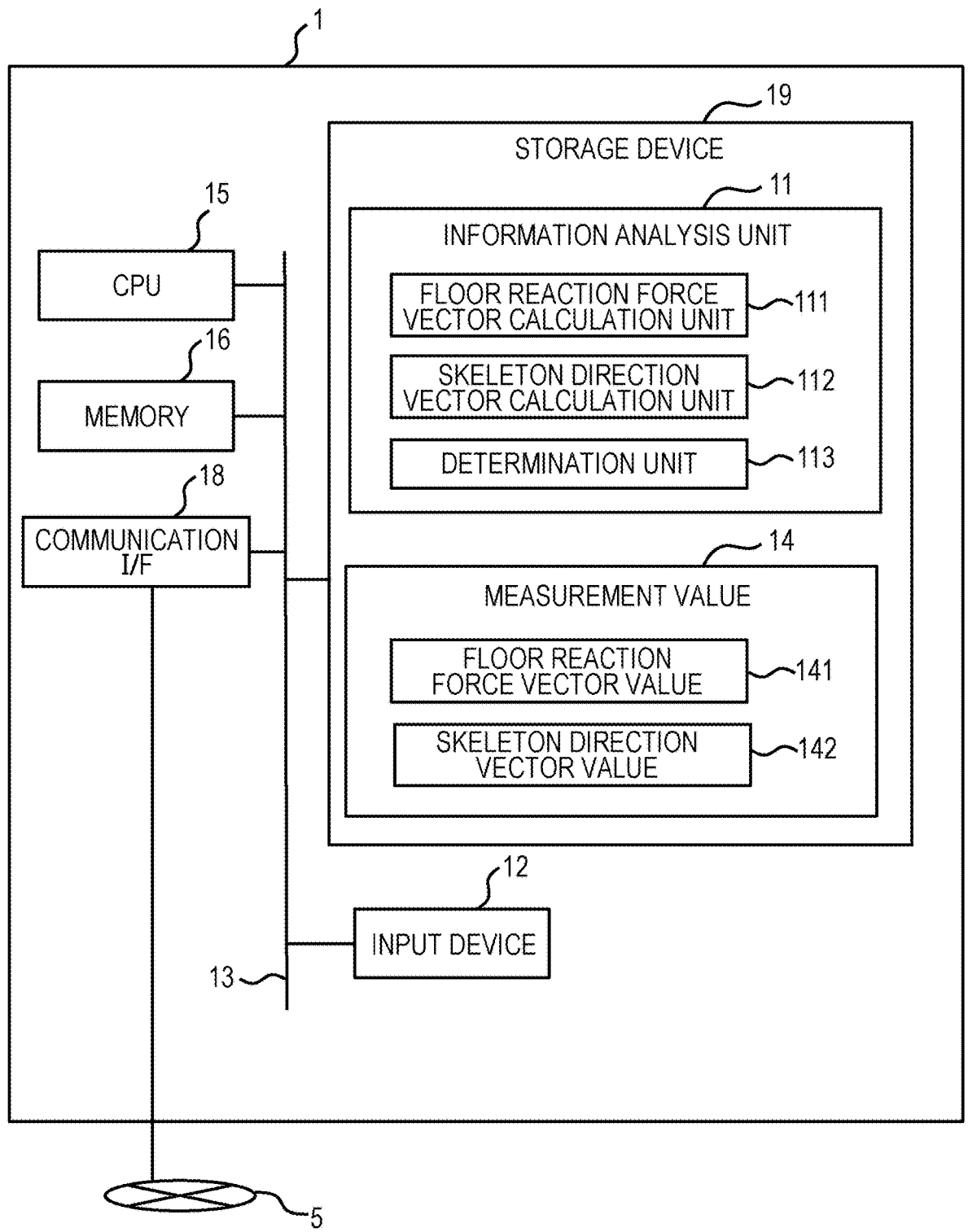

EACH COORDINATE: $L_1(Xl_1\ Yl_1), L_2(Xl_2\ Yl_2), \cdots L_8(Xl_8\ Yl_8)$
EACH PRESSURE VALUE: $Ml_1, Ml_2 \cdots Ml_8,$
PRESSURE BARYCENTRIC COORDINATE: $G(Xg\ Yg)$ $Xg=(Xl_1 Ml_1+ Xl_2 Ml_2+ \cdots + Xl_8 Ml_8)/(Ml_1+Ml_2+ \cdots +Ml_8) \cdots$ EXPRESSION 1

$Yg=(Yl_1 Ml_1+ Yl_2 Ml_2+ \cdots + Yl_8 Ml_8)/(Ml_1+Ml_2+ \cdots +Ml_8) \cdots$ EXPRESSION 2

SKELETON

FIG. 14
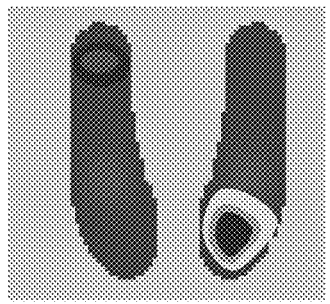
INITIAL CONTACT
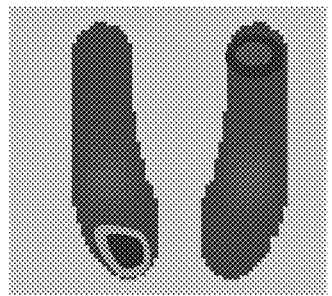
PRE SWING
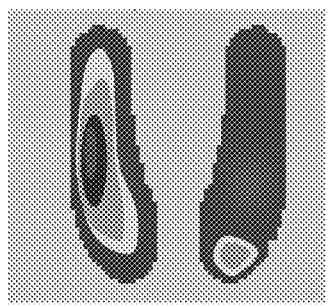
LORDING RESPONSE
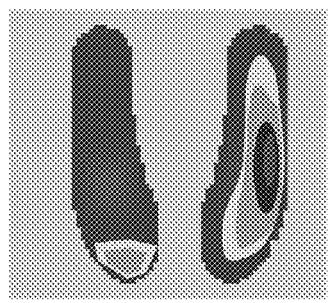
INITIAL SWING
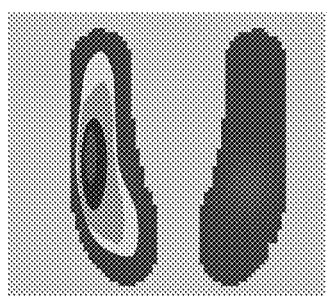
MID STANCE
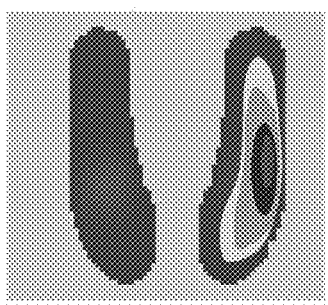
MID SWING
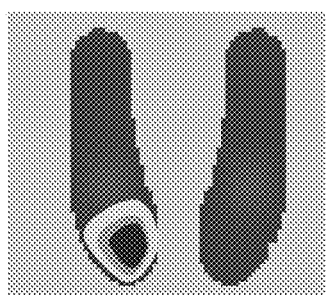
TERMINAL STANCE
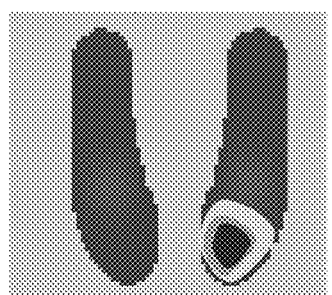
TERMINAL SWING

BIOMETRIC SYSTEM AND METHOD

BACKGROUND OF THE INVENTION

1. Field of the Invention

The present invention relates to a biometric technique that supports walk training.

2. Description of the Related Art

At medical and nursing care facilities, therapists and caregivers observe conditions of patients during walk training, and give instructions on how to balance. However, since verbal instructions are difficult to understand, it is necessary to have a system that visualizes the situation of balance and presents the walk situation in an easily recognizable manner.

JP 2012-176170 A discloses a technique that realizes health maintenance and care including foot-part balance correction and fall prevention. JP 2012-176170 A discloses a technique that provides functional and effective training necessary for balance correction by evaluating the function of a hallux, the function of a thenar part, and the function of a hypothenar part, which are important for balance correction, from the pressure variations from a heel part.

Patent Literature 1: JP 2012-176170 A

SUMMARY OF THE INVENTION

The technique described in JP 2012-176170 A can display the balance of foot pressure and the body position as to which part of the foot the pressure is applied, but the technique has had a problem of difficulty in understanding the direction in which the foot pressure is applied during walking. In addition, a cane is used for walk training, but it has been difficult to verbally understand how to balance with a device such as a cane.

Therefore, an object of the present invention is to provide a biometric system and method capable of presenting more stable walking support by estimating a floor reaction force vector from foot pressure and simultaneously displaying the skeleton direction of the foot.

In one embodiment, a biometric system for solving the above problems has a camera that captures a subject, a pressure information collection unit that detects a pressure value of at least one sole of the subject, a skeleton direction vector calculation unit that calculates a skeleton direction vector of the subject captured by the camera, a floor reaction force vector calculation unit that calculates a floor reaction force vector on the basis of information on pressure from the pressure information collection unit, and an analysis result output unit that displays, in a superimposing manner, the skeleton direction vector calculated by the skeleton direction vector calculation unit and the floor reaction force vector calculated by the floor reaction force vector calculation unit.

According to the present invention, it is possible to more efficiently grasp the walk state and the posture state. Reduction in the burden on the staff has an effect of allowing the staff to give explanations and instructions in a shorter time.

BRIEF DESCRIPTION OF THE DRAWINGS

FIG. 2 is a hardware block diagram of an information processing unit according to the first embodiment;

FIG. 14 is a view illustrating a calculation example of a walk cycle from the foot pressure sensor according to a fourth embodiment;

DESCRIPTION OF THE PREFERRED EMBODIMENTS

Embodiments

Figure 1:
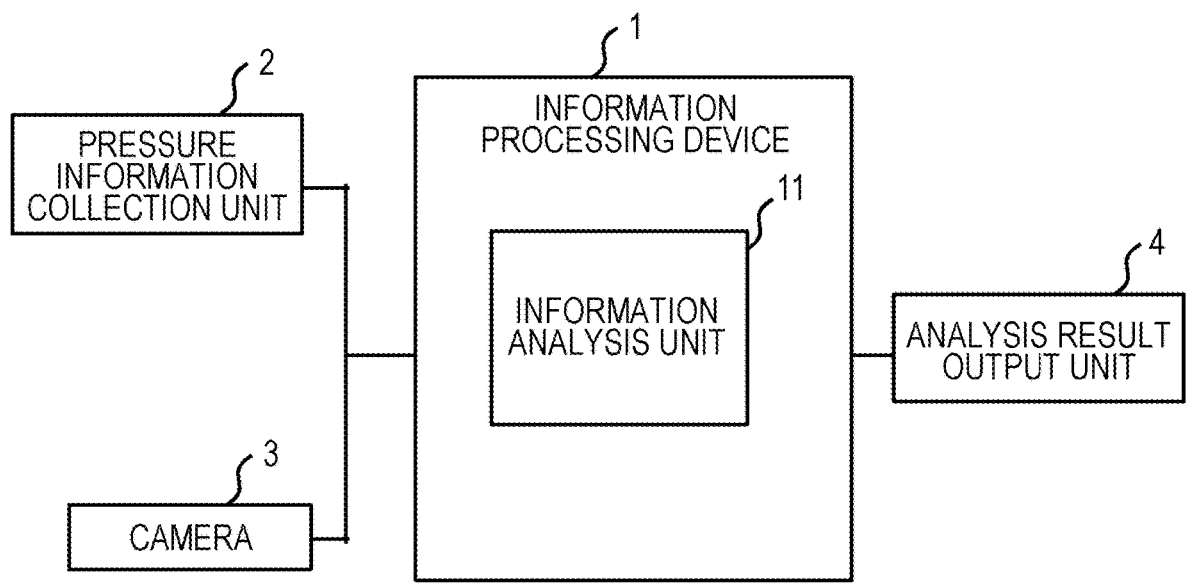
FIG. 1 is an overall configuration diagram of a biometric system according to a first embodiment.

Embodiments of the present invention will be described below with reference to the drawings. Each embodiment is an example for explaining the present invention, and is omitted or simplified as appropriate for a clearer description. The present invention can also be carried out in various other forms. Unless otherwise specified, each component may be singular or plural.

The position, size, shape, range, and the like of each component presented in the drawings do not necessarily represent the actual position, size, shape, range, and the like, for the purpose of facilitating understanding of the invention. Therefore, the present invention is not necessarily limited to the positions, sizes, shapes, ranges, and the like disclosed in the drawings.

As an example of various types of information, the database may include "table", "list", and "queue", and various types of information may be expressed by other data structures. For example, various types of information such as "XX table", "XX list", and "XX queue" may be referred to as "XX information". In describing the identification information, expressions such as "identification information", "identifier", "name", "ID", and "number" are used, and these can be replaced with one another.

When a plurality of components having the identical or similar functions exists, the identical reference numerals are sometimes attached with different suffixes for explanations. When it is not necessary to distinguish among these components, the suffixes may be omitted in explanations.

In an embodiment, processing performed by executing a program is sometimes explained. Here, the computer executes the program by the processor (e.g., CPU and GPU), and performs the processing determined by the program using a storage resource (e.g., memory), an interface device (e.g., communication port), and the like. Therefore, the subject of processing performed by executing the program may be a processor. Similarly, the subject of processing performed by executing the program may be a controller, a device, a system, a computer, or a node having a processor. The subject of processing performed by executing the program is only required to be an arithmetic unit, and may include a dedicated circuit that performs specific processing. Here, the dedicated circuit is, for example, a field programmable gate array (FPGA), an application specific integrated circuit (ASIC), a complex programmable logic device (CPLD), and the like.

The program may be installed into the computer from a program source. The program source may be, for example, a program distribution server or a computer-readable storage medium. When the program source is a program distribution server, the program distribution server may include a processor and a storage resource that stores a program to be distributed, and the processor of the program distribution server may distribute to another computer the program to be distributed. In the embodiment, two or more programs may be implemented as one program, and one program may be implemented as two or more programs.

First Embodiment

FIG. 1 is an overall configuration diagram of a biometric system used for walk support according to the embodiment.

An information processing device 1 receives information on pressure from a pressure information collection unit 2 and receives image information of a subject from a camera 3. An information analysis unit 11 obtains a floor reaction force vector of the subject on the basis of information on pressure to be input from the pressure information collection unit 2. Instead of the floor reaction force vector, a pressure barycenter position may be obtained. Furthermore, the information analysis unit 11 receives an image of the subject acquired by the camera 3 and detects the skeleton of the subject from the image of the subject. The information analysis unit 11 synchronizes the information of the floor reaction force vector obtained from the information on the pressure received from the pressure information collection unit 2 with the information of the skeleton of the subject detected from the image of the subject acquired from the camera 3, and outputs a time series change of the floor reaction force vector and the skeleton of the subject to an analysis result output unit 4.

The information processing device 1 is a computer including a communication I/F, a processing unit (hereinafter, CPU), a memory, and a storage device. Details will be described with reference to FIG. 2.

The pressure information collection unit 2 collects pressure information from, for example, a pressure sensor unit provided on the sole of the subject person or a shoe insole or a shoe insert of the subject person, and outputs the pressure information to the information processing device 1. Details will be described with reference to FIG. 3A and the like. Here, a force sensor or another kinesthetic sensor may be used.

The camera 3, which is one or a plurality of cameras, captures the subject and outputs a captured video to the information processing device 1. For example, by using two cameras, and placing one camera in front of or behind the subject, and placing the other camera in the left or right direction of the subject, it is possible to grasp the subject in a three-dimensional space.

The analysis result output unit 4 includes a display device, for example, and outputs the analysis result of the information processing device 1 to the user.

FIG. 2 is a diagram presenting an example of the hardware configuration of the information processing device 1 of the biometric system. The information processing device 1 includes one or a plurality of computers. Each component of the hardware of the information processing device 1 may be singular or plural. The information processing device 1 includes, for example, a CPU 15 serving as a processing unit, a communication I/F 18 operating as a communication unit that communicates with an external device, a storage device 19, and a memory 16.

The CPU 15 operates as a processing unit, and inputs information from the pressure information collection unit 2 and the camera 3 via the communication I/F 18. The storage device 19 may store a program to be executed by the CPU 15 and may also hold a database that stores measurement results of the subject. The communication I/F 18 inputs information from the pressure information collection unit 2 and the camera 3, and outputs the analysis result of the information processing device 1 to the analysis result output unit 4.

The processing unit may be an arithmetic unit or a control unit, and may include a processor such as a central processing unit (CPU) or a graphics processing unit (GPU), or may include a dedicated circuit that performs specific processing. Here, the dedicated circuit is, for example, a field programmable gate array (FPGA), an application specific integrated circuit (ASIC), a complex programmable logic device (CPLD), and the like.

An input device 12 may be, for example, an interface that receives data from an external device, a mouse, a keyboard, or the like.

The memory 16 stores a program stored in the storage device 19 and data processed by the CPU 15. The memory 16 is constituted with, for example, a DRAM or an SDRAM.

The storage device 19 is constituted by a nonvolatile memory such as an HDD or an SSD, and stores various programs, pressure information, and skeleton information. As various programs, a floor reaction force vector calculation program for calculating a floor reaction force vector of the subject on the basis of information on pressure to be input from the pressure information collection unit 2, and a skeleton direction vector calculation program in which an image of the subject acquired by the camera 3 is input, the skeleton of the subject is detected from the input subject image, and the skeleton direction vector is calculated from the detected skeleton are stored.

In order to facilitate understanding of the explanation, the functions implemented when the CPU 15 executes the floor reaction force vector calculation program and the skeleton direction vector calculation program will be hereinafter referred to as a floor reaction force vector calculation unit 111 and a skeleton direction vector calculation unit 112, respectively.

The CPU 15, the memory 16, the communication I/F 18, the input device 12, and the storage device 19 are interconnected via a bus 13.

A network 5 may be a wired network or a wireless network connected via a wireless access point. The information processing device 1 may be connected with the pressure information collection unit 2, the camera 3, and the analysis result output unit 4 via the network 5.

Figures 3A, 3B:
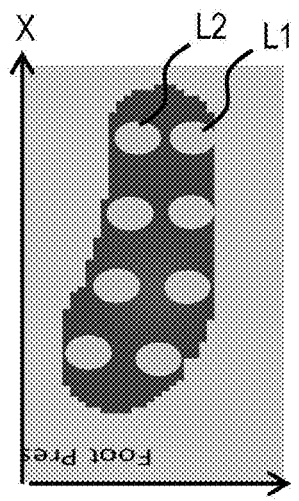
FIG. 3A is a view for explaining a pressure sensor unit constituting a pressure information collection unit according to the first embodiment.
FIG. 3B is expressions for explaining how to obtain a pressure barycentric coordinate of a foot according to the first embodiment.

FIG. 3A is a view for explaining the pressure sensor unit constituting the pressure information collection unit according to the first embodiment. The pressure information collection unit 2 is constituted with a plurality of sensors provided to an insert of the shoe worn by the subject person, for example. The pressure information collection unit 2 acquires a pressure value by a plurality of sensors. For example, in FIG. 3A, eight sensors are provided in the pressure sensor unit to measure the pressure of the left sole. The sensors are given identifiers L1 to L8, respectively, and given coordinates specifying the position where each sensor is installed.

For example, coordinates are given to each of the eight sensors such that the coordinates of the sensor of L1 are (X11 Y11) and the coordinates of the sensor of L2 are (X12 Y12).

The pressure value measured by each sensor is output as M11, M12, . . . M18.

The pressure sensor unit illustrated in FIG. 3A is the pressure sensor unit for the left foot of the subject person, and the pressure sensor unit for the right foot acquires the pressure value of the right sole by the eight sensors having identifiers R1 to R8. Similarly to the left foot, coordinates are given to each of the eight sensors such that the coordinates of the sensor of R1 are (XR1 YR1) and the coordinates of the sensor of R2 are (XR2 YR2). The pressure value measured by each sensor for the right foot is output as MR1, MR2, . . . MR8.

FIG. 3B presents how to obtain the pressure barycentric coordinate of the foot (left foot). The coordinates of the pressure barycenter of the foot of an x-axis are calculated by Expression 1, and the coordinates of the pressure barycenter of the foot of a y-axis are calculated by Expression 2. The floor reaction force vector calculation unit 111 calculates the pressure barycenter by Expressions 1 and 2 from the coordinate value of each pressure sensor and the pressure value measured by each pressure sensor. The x-axis and the y-axis are coordinates provided on a horizontal plane. In the first embodiment, the pressure barycenter of the foot (left foot) is sometimes referred to as a first pressure barycenter.

Figure 4:
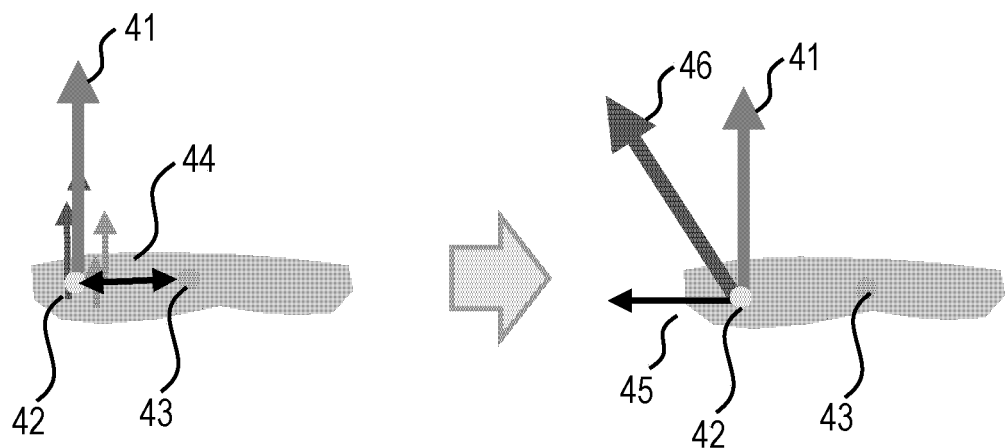
FIG. 4 is a view illustrating the calculation principle of a floor reaction force vector according to the first embodiment.

FIG. 4 is a view illustrating the calculation principle of the floor reaction force vector according to the first embodiment. FIG. 4 presents on its left side a pressure barycenter 42, a sole barycenter 43, a distance 44 between the pressure barycenter 42 and the sole barycenter 43, and a pressure vector 41 obtained from the sum of the pressure values detected by the eight sensors. The sole barycenter 43 is a barycenter uniformly obtained in accordance with the size of the foot. FIG. 4 presents a state in which the pressure barycenter 42 is located on the toe side relative to the sole barycenter 43 and force is applied only to the toe.

FIG. 4 presents on its right side the calculation principle of the floor reaction force vector. A floor reaction force vector 46 is obtained by adding two vectors of a barycenter vector 45 obtained from the distance between the sole barycenter 43 and the first pressure barycenter 42 and the pressure vector 41 obtained from the total value of the first pressure barycenter 42 and the pressure value.

The information processing device 1 may receive the pressure information of each of the right and left feet from the pressure information collection unit 2, obtain the floor reaction force vector 46 of each of the right and left, and store them in the storage device 19 as a floor reaction force vector value 141 as time series information.

Figure 5:
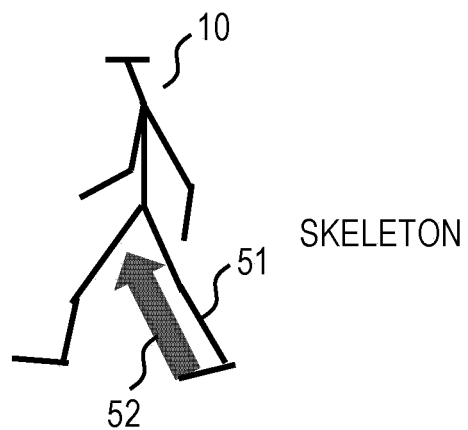
FIG. 5 is a view illustrating a calculation example of a skeleton direction vector according to the first embodiment.

FIG. 5 is a view illustrating a calculation example of the skeleton direction vector by the skeleton of the subject person acquired by the camera 3. The skeleton direction vector calculation unit 112 is implemented by using a skeleton detection algorithm such as OpenPose. OpenPose, released by Carnegie Mellon University (CMU) at Conference on Computer Vision and Pattern Recognition, 2017, is a technology for detecting keypoints (feature points) and estimating the relationship between keypoints. Using a skeleton 51 calculated from an image captured by the camera 3, OpenPose calculates a direction vector of a lower limb skeleton of the subject person as a skeleton direction vector 52. It is to be noted that, not limited to OpenPose, another skeleton detection algorithm may be used here.

Figure 6:
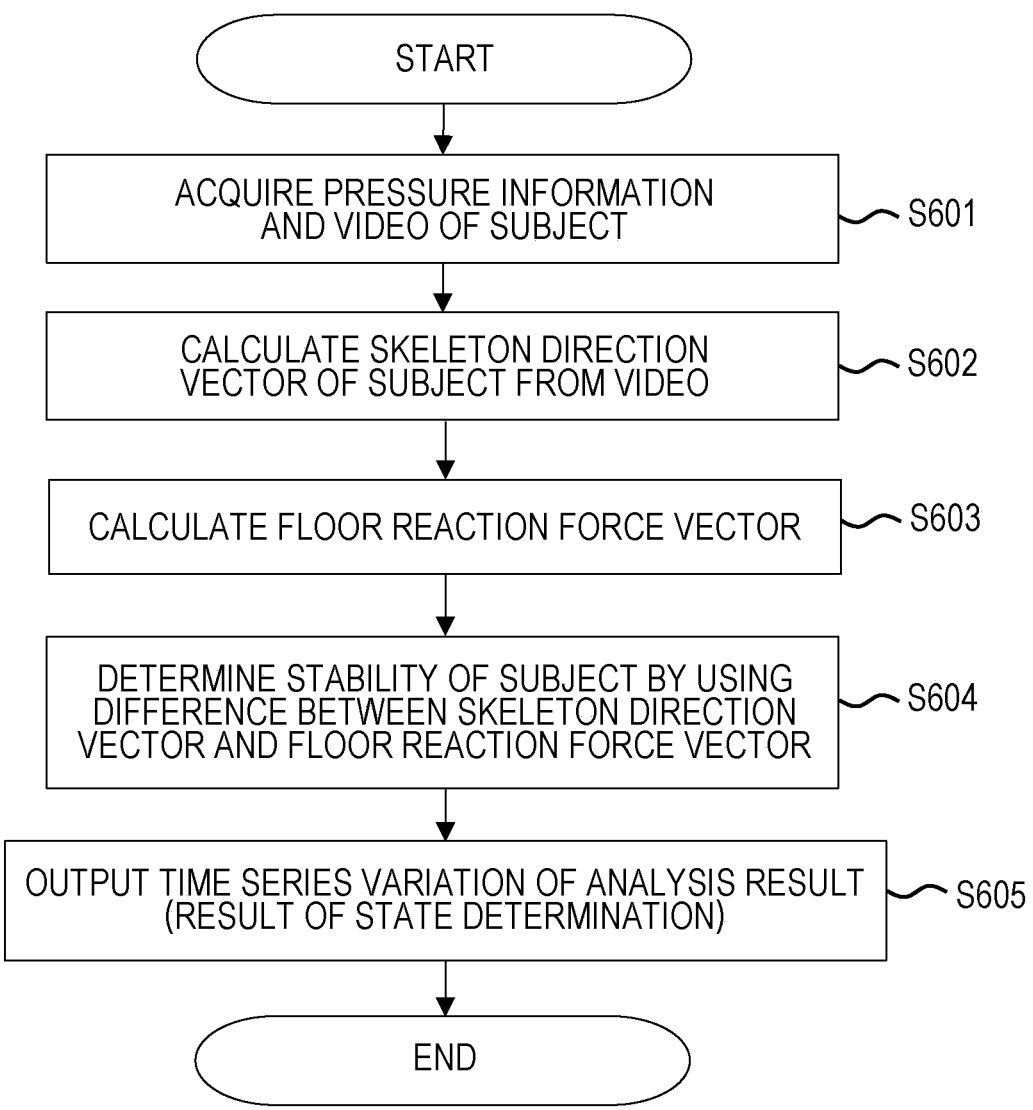
FIG. 6 is a flowchart to be executed by the biometric system according to the first embodiment.

FIG. 6 is a flowchart to be executed by the biometric system according to the first embodiment.

Upon starting the processing, in step S601, the floor reaction force vector calculation unit 111 of the information analysis unit 11 acquires the pressure information of the subject having walked from the pressure information collection unit 2. The skeleton direction vector calculation unit 112 acquires a video of the subject captured by the camera 3.

In step S602, the skeleton direction vector calculation unit 112 detects the skeleton of the subject from a video of a scene of walk of the subject captured by the camera 3, and calculates the skeleton direction vector of the lower limb skeleton. The calculation method of the skeleton direction vector is as described in FIG. 5.

In step S603, the floor reaction force vector calculation unit 111 calculates the floor reaction force vector on the basis of the information on the pressure received from the pressure information collection unit 2. The calculation method of the floor reaction force vector is as described in FIGS. 3A, 3B, and 4. It is to be noted that the order of steps S602 and S603 may be reversed.

In step S604, a determination unit 113 of the information analysis unit 11 determines the stability of the subject using a difference between the skeleton direction vector and the floor reaction force vector. Details of the determination will be described with reference to FIG. 7.

In step S605, with the determination result of the state of the subject as an analysis result, the information analysis unit 11 outputs a time series change of the analysis result to the analysis result output unit 4. The analysis result output unit 4 displays, in a superimposing manner, the skeleton direction vector calculated by the skeleton direction vector calculation unit 112 and the floor reaction force vector calculated by the floor reaction force vector calculation unit 111. As presented in FIG. 7, the analysis result output unit 4 displays, in a superimposing manner, a difference 71 between the skeleton direction vector 52 and the floor reaction force vector 46 in addition to the skeleton direction vector 52 and the floor reaction force vector 46. Here, for example, a vertical axis may be displayed in a superimposing manner together with the skeleton display. This can clearly present how much extent the leg skeleton or the trunk is inclined with respect to the vertical axis, for example.

Visual feedback of this to the subject helps the self posture recognition of the subject and is effective for spontaneous posture correction.

Figure 7:
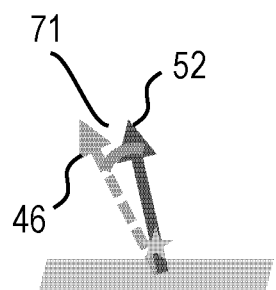
FIG. 7 is a view illustrating an operation of a determination unit according to the first embodiment.

FIG. 7 illustrates the operation of the determination unit 113 in step S604 of FIG. 6.

When a subject 10 is captured by the two cameras from the both directions of the front and back and the right and left, it is possible to grasp the skeleton direction vector 52 in a three-dimensional direction. The determination unit 113 temporally synchronizes the outputs of the floor reaction force vector calculation unit 111 and the skeleton direction vector calculation unit 112. This is for the purpose of temporally aligning and comparing at the same time the video captured by the camera and the information on the pressure detected by the pressure information collection unit 2. When the floor reaction force vector value 141 and a skeleton direction vector value 142 are stored in a measurement value 14, they may be stored together with time stamp information, and the determination unit 113 may read the floor reaction force vector value 141 and the skeleton direction vector value 142 having the identical time stamp.

The determination unit 113 outputs the skeleton direction vector 52 and the floor reaction force vector 46 at the identical time to the analysis result output unit 4 via the communication I/F 18. FIG. 7 illustrates an output example of the analysis result output unit 4. As illustrated in FIG. 7, the skeleton direction vector 52 and the floor reaction force vector 46 having been synchronized are displayed in a superimposing manner to grasp the difference 71 between them. This difference 71 can be expressed by an angle difference between the skeleton direction vector 52 and the floor reaction force vector 46 in a three-dimensional space.

Figure 8:
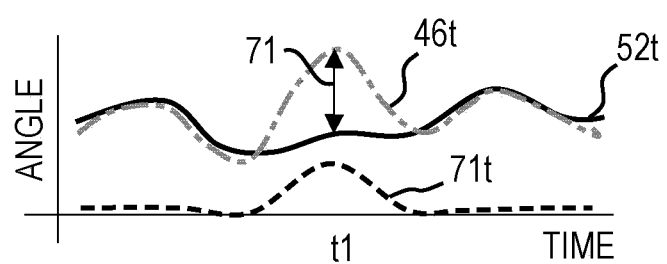
FIG. 8 is a chart presenting a time series change of the floor reaction force vector and the skeleton direction vector according to the first embodiment.

FIG. 8 is a chart presenting a time series change of the floor reaction force vector and the skeleton direction vector according to the first embodiment. As presented in FIG. 8, a time series change of the floor reaction force vector value 141 and the skeleton direction vector value 142 having been synchronized to be output from the determination unit 113 is presented. FIG. 8 presents a time series change 52*t* of the skeleton direction vector value, a time series change 46*t* of the floor reaction force vector value, and a time series change 71*t* of the difference. It is to be noted that the time series change is displayed by the analysis result display unit 4 from the determination unit via the communication I/F 18. This allows the user to understand timing with a large difference (time t1). It is to be noted that if the video from the camera 3 is stored in the storage device 19 and the outputs from the floor reaction force vector calculation unit 111 and the skeleton direction vector calculation unit 112 are synchronized with the stored video by the determination unit 113, it is possible to output the video at the time t1 to the analysis result output unit 4. The user can confirm, also with video, the timing at which the difference between the skeleton direction vector and the floor reaction force vector is large.

While FIGS. 3A to 8 present the left foot, which is one leg of the subject, it is possible to similarly display the floor reaction force vector and the skeleton direction vector also for the right leg of the subject. The difference between the floor reaction force vector and the skeleton direction vector can be displayed in a superimposing manner by the analysis result output unit 4.

In that case, the pressure information collection unit 2 detects the pressure values of the soles of the both feet of the subject by using a plurality of pressure sensors as illustrated in FIG. 3A installed on the soles of the both right and left feet.

The floor reaction force vector calculation unit 111 calculates the floor reaction force vectors of the right and left feet as a left foot floor reaction force vector and a right foot floor reaction force vector from information on the pressure of the right and left soles of the subject.

The analysis result output unit displays, in a superimposing manner, the left foot skeleton direction vector calculated by the skeleton direction vector calculation unit 112 and the left foot floor reaction force vector. In addition, the analysis result output unit displays, in a superimposing manner, the right foot skeleton direction vector calculated by the skeleton direction vector calculation unit 112 and the right foot floor reaction force vector.

The determination unit 113 determines the stability of the left foot from the difference between the left foot skeleton direction vector and the left foot floor reaction force vector. In addition, the determination unit 113 determines the stability of the right foot from the difference between the right foot skeleton direction vector and the right foot floor reaction force vector.

Figure 9:
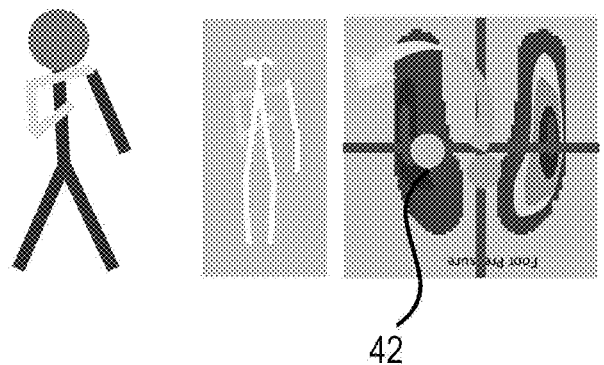
FIG. 9 is a view displaying a skeleton and a pressure value in a state where the balance of a subject according to the first embodiment is lost.

FIG. 9 is a view displaying the skeleton and the pressure value in a state where the balance of the subject according to the first embodiment is lost. The display presented in FIG. 8 allows the user to understand that the time t1 is the timing at which the difference between the skeleton direction vector 52 and the floor reaction force vector 46 is the largest. When information specifying the time t1 is input, the determination unit 113 reads the skeleton direction vector at the time t1 from the skeleton direction vector value 142, reads the floor reaction force vector at the time t1 from the floor reaction force vector value 141, and outputs them to the analysis result output unit 4. As illustrated in FIG. 9, the analysis result output unit 4 simultaneously displays the skeleton of the subject, the pressure value balance, and the pressure barycenter 42 at the time t1 of the timing at which the difference 71 is large.

This allows the user to easily understand the posture and the pressure barycenter at the timing at which the difference 71 becomes large, and hence the user can easily correct the posture.

Figure 10:
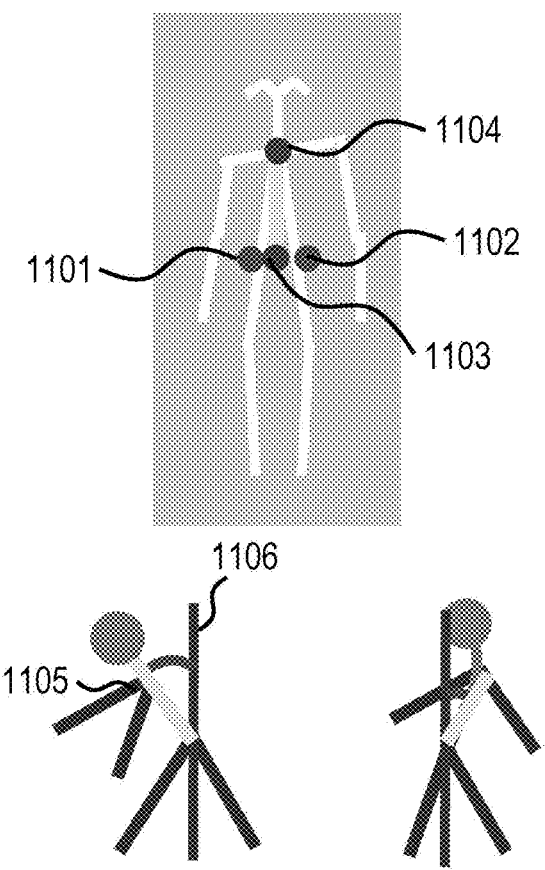
FIG. 10 is a view displaying another state where the balance of the subject according to the first embodiment is lost.

FIG. 10 is a view displaying another state where the balance of the subject according to the first embodiment is lost. The skeleton direction vector calculation unit 112 analyzes the video from the camera 3, calculates the inclination of the upper limb of the subject, and outputs it to the analysis result output unit 4.

The analysis result output unit 4 simultaneously displays the skeleton direction vector, the floor reaction force vector, and the inclination of the upper limb. By displaying both of a line 1104 indicating the inclination of the upper limb connecting the neck and a center position 1103 connecting a joint position 1101 of the right hip of the upper limb and a joint position 1102 of the left hip of the upper limb, and the vertical axis of a skeleton center 1105 as auxiliary lines, it is possible to display whether the skeleton is inclined forward or backward and the inclination to the right and left, thereby allowing the user to easily understand the cause of the difference.

Second Embodiment

Figure 11:
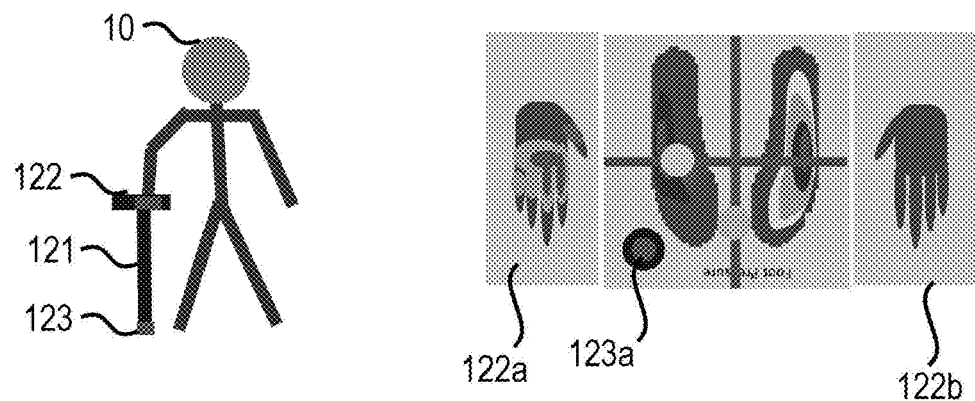
FIG. 11 is a view illustrating a display example of the skeleton and the pressure value when a cane according to a second embodiment is used.

FIG. 11 is a view illustrating a display example of the skeleton and the pressure value when a cane according to the second embodiment is used. In the first embodiment, the subject 10 performs walk training without a cane, while in the second embodiment, as shown in the left side of FIG. 11, the subject 10 performs walk training with a cane 121.

In the second embodiment, the pressure information collection unit 2 of FIG. 1 includes, in addition to the pressure sensor unit of the sole illustrated in FIG. 3A, a hand pressure sensor 122 that supports the cane 121, and a cane pressure sensor 123 at a position where the cane touches the ground. This embodiment is similar to the first embodiment except that the hand pressure sensor 122 and the cane pressure sensor 123 are added to process information on the pressure by the added sensors.

The pressure distribution detected by each pressure sensor is output to the analysis result output unit 4 by the information analysis unit 11, and is displayed as illustrated on the right side in FIG. 11. The hand pressure sensor is presented by a right hand pressure distribution 122a by a right hand pressure sensor and a left hand pressure distribution 122b by a left hand pressure sensor, and the pressure distribution of the cane and sole is presented as a cane-sole pressure distribution 123a.

Figure 12:
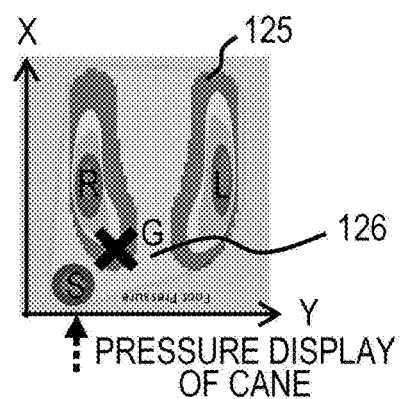
FIG. 12 is a view illustrating a display example of a base of support according to the second embodiment.

FIG. 12 is a view illustrating a display example of a base of support according to the second embodiment. FIG. 12 illustrates a relationship between a base of support 125 and the pressure distribution of the subject displayed by the analysis result output unit 4.

The base of support 125 in the case of having a cane is stored in the storage device 19, and the base of support 125 is displayed on the analysis result output unit 4.

The determination unit 113 obtains a second pressure barycenter 126 from the pressure values of the cane and the sole, and determines the stability of the subject in accordance with whether the second pressure barycenter is within the base of support. As for the second pressure barycenter, the pressure barycentric coordinate is obtained by adding the pressure and coordinates of the cane to the pressure barycenter of the foot described in FIG. 3A.

The determination unit 113 outputs a fall prediction alarm to the analysis result output unit 4 when the barycenter of the subject deviates from the base of support 125. It is to be noted that the base of support 125 represents a region in which the barycenter of the subject is stable when it is within the range thereof and is less likely to fall.

It is to be noted that also in the second embodiment, the floor reaction force vector and the skeleton direction vector of the subject may be displayed in a superimposing manner on the analysis result output unit 4 on the basis of the information on the pressure from the pressure sensor unit of the sole.

As described above, according to the second embodiment, it is possible to effectively support the walk training of the subject in need of a cane.

Third Embodiment

Figure 13:
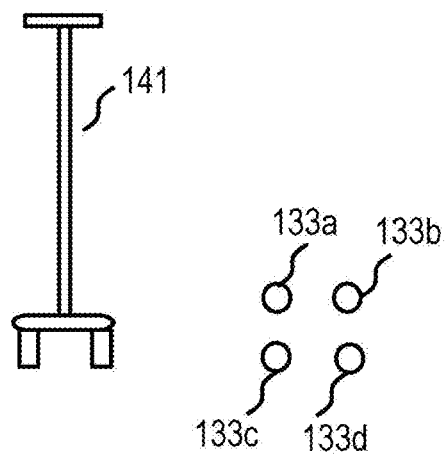
FIG. 13 is a view illustrating an arrangement of a pressure sensor of a four-point supported cane according to a third embodiment.

FIG. 13 is a view illustrating the arrangement of a pressure sensor of a four-point supported cane according to the third embodiment. Ground contact surfaces of four support shafts are provided with four cane pressure sensors 133a, 133b, 133c, and 133d, respectively.

In the third embodiment, the floor reaction force vector of the cane (cane floor reaction force vector) can be calculated by the four sensors as the eight sole sensors of FIG. 3A. That is, the sole barycenter 43 of FIG. 4 becomes a cane barycenter, which is the center point of the four-point support of the cane, the values of the four pressure sensors correspond to the values of the pressure value M11 and the like of FIG. 3A, and the cane pressure barycenter is obtained from the values of the four pressure sensors and the coordinates of the four pressure sensors. A cane barycenter vector is calculated from the distance between a cane barycenter and a cane pressure barycenter, and a cane pressure vector is calculated from the cane pressure barycenter and the sum of the four pressure sensors. Then, a value obtained by adding two vectors of the cane barycenter vector and the cane pressure vector is calculated as a cane floor reaction force vector.

It is to be noted that also in the third embodiment, the floor reaction force vector and the skeleton direction vector of the subject may be displayed in a superimposing manner on the analysis result output unit 4 on the basis of the information on the pressure from the pressure sensor unit of the sole.

A cane direction vector and the cane floor reaction force vector of the cane 121 may be displayed in a superimposing manner on the analysis result output unit 4.

Since walk training using a cane is an important step for a subject with severe disability, according to the third embodiment, walk training using a cane is effective in walk training for the subject with severe disability. Furthermore, it has an effect that the state of the subject can be quickly presented to the medical and nursing staff.

As described above, the present invention can provide a biometric system and method capable of presenting more stable walking support by estimating a floor reaction force vector from foot pressure and simultaneously displaying the skeleton direction of the foot.

In addition, it becomes possible to easily understand how to balance an instrument such as a cane that is used in walk training.

Fourth Embodiment

In the fourth embodiment, a walk cycle can be estimated and presented from the position of the pressure barycenter 42 obtained from the value of each pressure sensor and time series information thereof. The walk cycle is defined by the time from the initial contact of an ipsilateral foot to the next initial contact, for example. For example, it is also possible to easily calculate by analyzing a time series change of an output of a pressure sensor installed on a heel part and calculating the interval of time at which the pressure starts to be applied. Furthermore, the walk cycle can be subdivided. For example, according to the definition of gait analysis published by Rancho Los Amigos National Rehabilitation Center in 1992, the walk cycle is classified into the eight categories of initial contact (IC), lording response (LR) (from IC to contralateral toe off, mid stance (MSt) (from contralateral toe off to contralateral lower leg droop), terminal stance (TSt) (from contralateral lower leg droop to contralateral IC), pre swing (PSw) (from contralateral IC to observational limb toe off), initial swing (ISw) (from observational limb toe off to intersection of both lower legs), mid swing (MSw) (from intersection of both lower legs to lower leg droop), and terminal swing (TSw) (from lower leg droop to IC).

FIG. 14 illustrates an example of the pressure of the foot when classified into each phase of the walk cycle of the fourth embodiment. The presence or absence of pressure on both feet and sites on which pressure is applied such as a toe and a heel are recognized to estimate the phase (category) of the walk cycle.

The determination unit 113 calculates the walk cycle and phase from the coordinates of the pressure barycenter, and outputs them to the analysis result output unit 4. The analysis result output unit 4 displays, in a superimposing manner, the left foot skeleton direction vector calculated by the skeleton direction vector calculation unit 112 and the left foot floor reaction force vector, and displays, in a superimposing manner, the right foot skeleton direction vector calculated by the skeleton direction vector calculation unit 112, the right foot floor reaction force vector, and the walk cycle.

A stride length and a stride width can be estimated and presented by using information of the camera that detects the skeleton. Walk time in 10 meter walk can also be presented from the stride length.

Fifth Embodiment

Higher brain function data (results of simple tests for measuring brain functions) are input and myoelectric data are input for monitoring of the walk state (effect evaluation of rehabilitation), and information related to walking can be simultaneously presented in combination with the analysis results.

The determination unit 113 receives higher brain function data, myoelectric data, and a walk simulation moving image from an external device. The analysis result output unit 4 simultaneously displays the skeleton direction vector, the floor reaction force vector, and the data from the external device.

Sixth Embodiment

In the sixth embodiment, a walk simulation moving image 1201 serving as a sample of walk and information 1202 of the fourth embodiment and the fifth embodiment can be simultaneously presented by the analysis result output unit 4.

Figure 15:
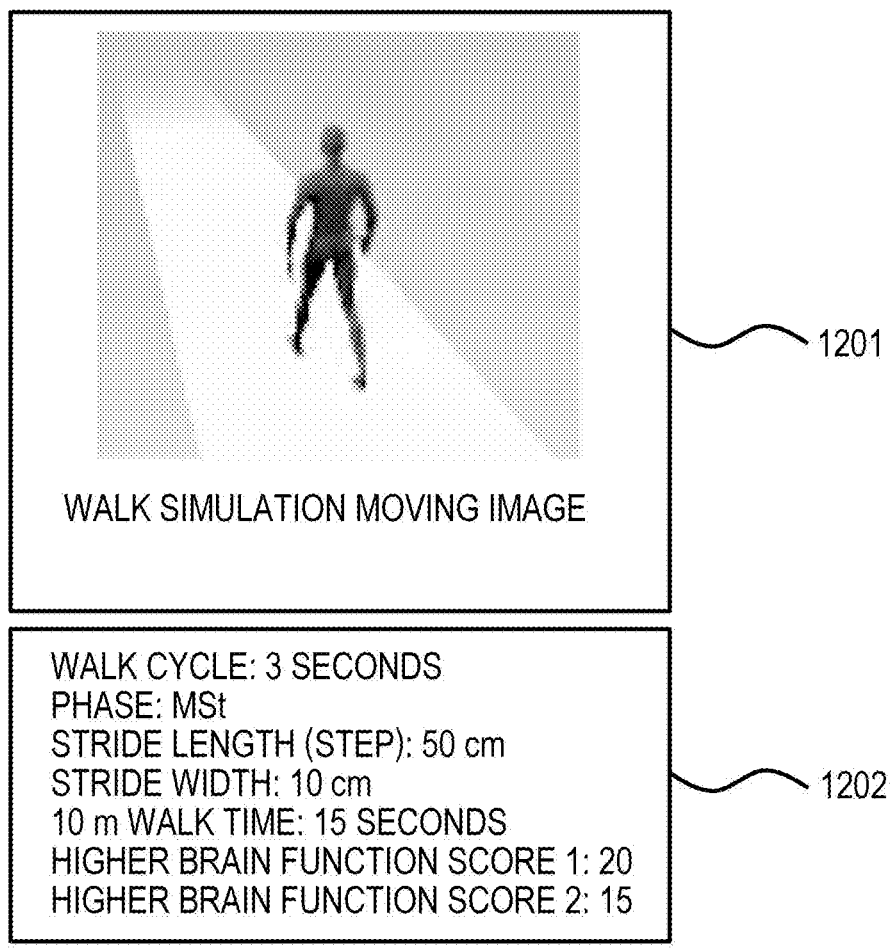
FIG. 15 is a view illustrating a display example of the walk cycle, phase, stride length, stride width, 10 m walk time, and higher brain function test results according to the fourth embodiment, a fifth embodiment, and a sixth embodiment.

FIG. 15 is an example of displaying the walk cycle of the fourth embodiment: 3 seconds, the phase of the walk cycle: Mst, the stride length: 50 cm, the stride width: 10 cm, the 10 m walk time: 15 seconds, and the higher brain function score 1 of the fifth embodiment: 20, and the higher brain function score 2: 15.

The determination unit 113 calculates the walk cycle, the phase, the stride length, the stride width, and the 10 m walk time of the subject on the basis of information from the skeleton direction vector calculation unit 112 and the pressure information collection unit 2. The analysis result output unit 4 displays the walk cycle, the phase, the stride length, the stride width, and the 10 m walk time.

Seventh Embodiment

In the seventh embodiment, the vertical axis extending from the pressure barycenter 42 position, the skeleton, and a foot pressure can be simultaneously displayed.

The skeleton direction vector calculation unit 112 calculates the knee joint position of the subject from the skeleton of the subject captured by the camera 3. The determination unit 113 calculates a horizontal distance 1302 between the vertical axis from the pressure barycenter 42 and the knee joint, and outputs the horizontal distance to the analysis result display unit 4. The analysis result output unit 4 displays, in a superimposing manner, the skeleton direction vector 52, the floor reaction force vector 46, and the horizontal distance 1302 of the knee joint.

In the seventh embodiment, the horizontal distance between the vertical axis extending from the pressure barycenter 42 position and the knee joint at the knee height can be simultaneously displayed on the analysis result output unit 4.

Figure 16:
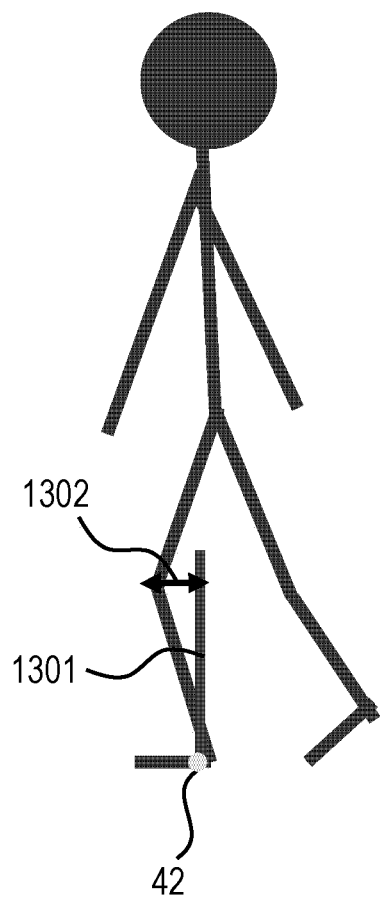
FIG. 16 is a view illustrating a calculation example of a horizontal distance between a vertical axis extending from a pressure barycenter and a knee joint according to a seventh embodiment.

FIG. 16 is an example of displaying the horizontal distance of the knee joint of the seventh embodiment. The knee joint can be calculated by the skeleton direction vector calculation unit 112. By presenting the horizontal distance 1302 between a vertical axis 1301 extending from the pressure barycenter 42 and the knee joint, it is possible to cause the user to easily understand the situation of flexion and extension of the knee for stable walk.

What is claimed is:

1. A biometric system comprising:
   a camera that captures a subject;
   a pressure information collection unit that detects a pressure value of at least one sole of the subject;
   a skeleton direction vector calculation unit that calculates a skeleton direction vector of the subject captured by the camera;
   a floor reaction force vector calculation unit that calculates a floor reaction force vector on a basis of information on pressure from the pressure information collection unit; and
   an analysis result output unit that displays, in a superimposing manner, the skeleton direction vector calculated by the skeleton direction vector calculation unit and the floor reaction force vector calculated by the floor reaction force vector calculation unit.

2. The biometric system according to claim 1 comprising:
   a determination unit that calculates a difference between the skeleton direction vector calculated by the skeleton direction vector calculation unit and the floor reaction force vector calculated by the floor reaction force vector calculation unit, wherein
   the analysis result output unit displays, in a superimposing manner, a difference between the skeleton direction vector and the floor reaction force vector calculated by the determination unit, in addition to the skeleton direction vector and the floor reaction force vector.

3. The biometric system according to claim 2, wherein
   the pressure information collection unit includes a plurality of pressure sensors that detects a pressure value from a sole of the subject, and
   the floor reaction force vector calculation unit calculates
   a first pressure barycenter of the subject from values of the plurality of pressure sensors,
   a barycenter vector from a distance between the first pressure barycenter and a sole barycenter of the subject,
   a pressure vector obtained from a sum of the first pressure barycenter and pressure values of the plurality of pressure sensors, and
   the floor reaction force vector by adding the barycenter vector and the pressure vector.

4. The biometric system according to claim 3, wherein
   each of the plurality of pressure sensors has a coordinate value for specifying a position at which each sensor is installed, and
   the floor reaction force vector calculation unit calculates coordinates of the first pressure barycenter by coordinate values of the plurality of pressure sensors and pressure values measured by the plurality of pressure sensors.

5. The biometric system according to claim 4, wherein
   the floor reaction force vector calculation unit calculates floor reaction force vectors of right and left feet as a right foot floor reaction force vector and a left foot floor reaction force vector from information on pressure of right and left soles, respectively, of the subject,
   the determination unit calculates a walk cycle and a phase from coordinates of the first pressure barycenter, and
   the analysis result output unit displays, in a superimposing manner, a left foot skeleton direction vector calculated by the skeleton direction vector calculation unit and the left foot floor reaction force vector, and displays, in a superimposing manner, a right foot skeleton direction vector calculated by the skeleton direction vector calculation unit, the right foot floor reaction force vector, and the walk cycle.

6. The biometric system according to claim 5, wherein the determination unit calculates the walk cycle, a phase, a stride length, a stride width, and a 10 m walk time of the subject on a basis of information from the skeleton direction vector calculation unit and the pressure information collection unit, and
the analysis result output unit displays the walk cycle, the phase, the stride length, the stride width, and the 10 m walk time.

7. The biometric system according to claim 3, wherein the pressure information collection unit has a cane pressure sensor provided at a tip of a cane, and
a cane-sole pressure distribution based on pressure values of the plurality of pressure sensors and the cane pressure sensor, and a base of support of the subject are displayed in a superimposing manner.

8. The biometric system according to claim 7, wherein the determination unit obtains a second pressure barycenter from pressure values of the cane and the sole, and determines stability of the subject in accordance with whether the second pressure barycenter is within the base of support.

9. The biometric system according to claim 7, wherein the cane is a four-point supported cane,
the cane pressure sensor is provided at each of the four-point supports, and
the floor reaction force vector calculation unit
obtains a cane pressure barycenter from values of the four cane pressure sensors provided at each of the four-cane supports and coordinates of the four cane pressure sensors,
calculates a cane barycenter vector from a distance between a cane barycenter of the cane and the cane pressure barycenter,
calculates a cane pressure vector from the cane pressure barycenter and a sum of the four cane pressure sensors, and
calculates, as a cane floor reaction force vector a value obtained by adding two vectors of the cane barycenter vector and the cane pressure vector.

10. The biometric system according to claim 2, wherein the determination unit temporally synchronizes the floor reaction force vector and the skeleton direction vector with each other, and outputs the result to the analysis result output unit, and
the analysis result output unit displays a time series change of the floor reaction force vector and the skeleton direction vector.

11. The biometric system according to claim 10, wherein the pressure information collection unit detects pressure values of both soles of feet of the subject,
the floor reaction force vector calculation unit calculates floor reaction force vectors of right and left feet as a right foot floor reaction force vector and a left foot floor reaction force vector from information on pressure of right and left soles, respectively, of the subject, and the analysis result output unit displays, in a superimposing manner, a left foot skeleton direction vector calculated by the skeleton direction vector calculation unit and the left foot floor reaction force vector, and displays, in a superimposing manner, a right foot skeleton direction vector calculated by the skeleton direction vector calculation unit and the right foot floor reaction force vector.

12. The biometric system according to claim 11, wherein the determination unit determines
stability of a left foot from a difference between the left foot skeleton direction vector and the left foot floor reaction force vector, and
stability of a right foot from a difference between the right foot skeleton direction vector and the right foot floor reaction force vector.

13. The biometric system according to claim 11, wherein the determination unit receives higher brain function data, myoelectric data, and a walk simulation moving image from an external device, and outputs the higher brain function data, the myoelectric data, and the walk simulation moving image to the analysis result output unit, and
the analysis result output unit simultaneously displays the skeleton direction vector, the floor reaction force vector, and data from the external device.

14. The biometric system according to claim 11, wherein the skeleton direction vector calculation unit calculates an inclination of an upper limb of the subject, and
the analysis result output unit simultaneously displays the skeleton direction vector, the floor reaction force vector, and the inclination of the upper limb.

15. The biometric system according to claim 11, wherein the skeleton direction vector calculation unit calculates a position of a knee joint of the subject,
the determination unit calculates a horizontal distance between a vertical axis from a pressure barycenter and the knee joint, and outputs the horizontal distance to the analysis result output unit, and
the analysis result output unit displays, in a superimposing manner, the skeleton direction vector, the floor reaction force vector, and the horizontal distance of the knee joint.

16. A biometric method comprising:
capturing a subject by a camera;
detecting a pressure value of at least one sole of the subject by a pressure information collection unit;
calculating, by a processing unit, a skeleton direction vector of the subject captured by the camera;
calculating, by the processing unit, a floor reaction force vector on a basis of information on pressure from the pressure information collection unit;
calculating, by the processing unit, a difference between the skeleton direction vector and the floor reaction force vector; and
displaying, by the processing unit, the skeleton direction vector, the floor reaction force vector, and a difference between the skeleton direction vector and the floor reaction force vector on an analysis result display unit in a superimposing manner.

* * * * *